United States Patent [19]
Badawy et al.

[11] Patent Number: 6,136,833
[45] Date of Patent: Oct. 24, 2000

[54] PHARMACEUTICAL FORMULATIONS AND PROCESS FOR THEIR PREPARATION

[75] Inventors: Sherif Ibrahim Farag Badawy, Wilmington, Del.; Donna Lynn Gilbert, Chadds Ford, Pa.

[73] Assignee: Dupont Pharmaceuticals Company, Wilmington, Del.

[21] Appl. No.: 09/228,261

[22] Filed: Jan. 11, 1999

Related U.S. Application Data

[60] Provisional application No. 60/071,712, Jan. 16, 1998.
[51] Int. Cl.⁷ .................. A61K 31/42; A61K 31/155; A61K 47/00
[52] U.S. Cl. ............ 514/378; 514/380; 514/631; 514/637; 514/784; 514/970
[58] Field of Search .................. 514/378, 380, 514/631, 637, 784, 970

[56] References Cited

U.S. PATENT DOCUMENTS 3,670,085  6/1972  Pryor et al. .................. 424/270

FOREIGN PATENT DOCUMENTS 9514683  6/1995  WIPO .
9638426  12/1996  WIPO .

OTHER PUBLICATIONS

Drugs of the Future, 22(5):508–517, 1997.
Remington's Pharmaceutical Sciences, 18th Edition, Mack Publishing Company, pp. 253–255, 1507–1508, 1990.
CA 87:189363, Larsen et al., 1977.
CA 89:204096, Zalipsky et al., 1978.
CA 104:213094, Chen et al., 1986.

*Primary Examiner*—Kimberly Jordan
*Attorney, Agent, or Firm*—Robert W. Black; Kenneth B. Rubin

[57] ABSTRACT

Provided is a pharmaceutical composition comprising a tablet or capsule containing a pharmacologically effective amount of a pharmaceutical compound, or a pharmaceutically acceptable salt thereof, having an amidine-based group and an optional ester group, a pharmaceutically acceptable solid carrier, and a pharmaceutically acceptable acid in an amount to modify the pH of the composition to substantially that of the compound at pH of maximum stability.

Such a composition is prepared by adding water during formulation manufacture and contacting the compound during formulation manufacture with a pharmaceutically acceptable acid having a pH in a saturated aqueous solution substantially that of the compound at pH of maximum stability.

3 Claims, No Drawings

PHARMACEUTICAL FORMULATIONS AND PROCESS FOR THEIR PREPARATION

This application claims the benefit of U.S. Provisional Application Ser. No. 60/071,712 filed on Jan. 16, 1998.

BACKGROUND OF THE INVENTION

1. Field Of Invention

This invention relates to pharmaceutical formulations and processes for their preparation and more particularly to such formulations and processes that provide stable products.

2. Prior Art

An article in Drugs of the Future 1997, 22(5): 508–517 describes many antithrombotic compounds under clinical or preclinical investigation, or appearing in published patent applications. Many of these compounds are IIb/IIIa receptor antagonists and most are characterized by the presence of ester-and/or amidine-based end groups. It has been observed that these compounds degrade into two main products-an ester hydrolysis product and/or an amidine hydrolysis product. Thus, there is a need to find pharmaceutical formulations of these compounds in which the compounds are stable over a reasonable shelf-life.

SUMMARY OF THE INVENTION

According to the present invention there is provided a pharmaceutical composition comprising a tablet, capsule or other solid dosage form containing a pharmacologically effective amount of a pharmaceutical compound, or a pharmaceutically acceptable salt thereof, having an amidine-based group and an optional ester group, a pharmaceutically acceptable solid carrier, and a pharmaceutically acceptable acid in an amount to modify the pH of the composition to substantially that of the compound at pH of maximum stability.

Also provided is a process for stabilizing a compound having an amidine-based group and an optional ester group, or a pharmaceutically acceptable salt thereof, against hydrolysis in a solid pharmaceutical formulation comprising: adding water during formulation manufacture and, contacting the compound during formulation manufacture with a pharmaceutically acceptable acid having a pH in a saturated aqueous solution substantially that of the compound at pH of maximum stability.

DETAILED DESCRIPTION OF THE INVENTION

This invention relates to the formulation and manufacturing process required to produce a stable solid dosage form containing a pharmaceutical compound, or a pharmaceutically acceptable salt thereof, which contains an optional carboxylic acid ester and an amidine group. The formulation contains a pH modifying agent(s) and the manufacturing process incorporates water.

The dosage form can be any solid dosage form including, but not limited to, tablet, capsule, pill, or sachet. These may also include granules and multi-layered tablets. In addition to the pharmaceutical compound and pH modifying agent(s), the formulation may contain other excipients (carriers) that are commonly used to aid in the production of the solid dosage form. These ingredients may include diluents (or fillers), binders, disintegrants, glidants, lubricants, antiadherents and/or coatings. Examples of ingredients include, but not limited to, lactose, sucrose, microcrystalline cellulose, starch, pregelatinized starch, dextrose, mannitol, fructose, xylitol, sorbitol, calcium sulfate, calcium phospate, calcium carbonate, polyvinylpyrrolidone, gelatin, methylcellulose, sodium carboxymethylcellulose, polyethylene glycol, stearate, magnesium carbonate, talc, stearic acid, sodium starch glycolate, crospovidone, and/or colloidal silicon dioxide. The formulations may also contain coloring agents, sweetening agents, and flavoring agents.

The term pharmaceutical compound is defined for purposes of this invention as any chemical compound having pharmacological activity which can be delivered from the solid dosage form to obtain a pharmacological result. The compound must contain an amidine group and may contain an ester group. Preferably both groups would be present. Examples of useful pharmaceutical compounds are disclosed in *Remington's Pharmaceutical Sciences*, 18th Edition, 1990, published by Mack Publishing Company, Eaton, Pa.; and in *The Pharmacological Basis of Therapeutics*, by Goodman and Gilman, 8th Edition, 1990, published by the Pergamon Press Inc., NY; and in *The Merck Index*, 12th Edition, 1996, published by Merck & Co., Whitehouse Station, N.J.; and in the aforesaid Drugs of the Future.

Preferred compounds are described in published PCT Application WO 95/14683, published Jun. 1, 1995, as the second embodiment. Preferred compounds described therein have the formula:

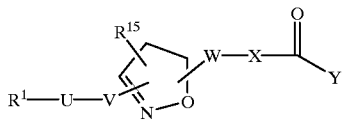

or a pharmaceutically acceptable salt thereof,
wherein:
$R^1$ is selected from $R^{2a}(R^3)N-$, $R^2(R^3)N(R^2N=)C-$, $R^{2a}(R^3)N(CH_2)_{p'}Z-$, $R^2(R^3)N(R^2N=)C(CH_2)_{p''}Z-$, $R^2(R^3)N(R^2N=)CN(R^2)-$, $R^2(R^3)NC(O)-$, $R^2(R^5O)N(R^2N=)C-$, $R^2(R^3)N(R^5ON=)C-$;

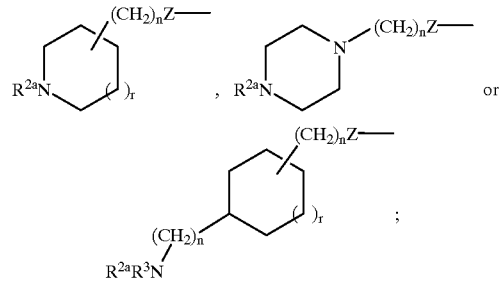

Z is selected from a bond, O, or S;
$R^2$ and $R^3$ are independently selected from: H; $C_1$–$C_6$ alkyl; $C_7$–$C_{11}$ arylalkyl optionally substituted with 0–3 groups selected from hydroxy, halogen, $C_1$–$C_6$ alkoxy, $C_1$–$C_6$ alkyl, $CF_3$, $S(O)_mCH_3$, $-N(CH_3)_2$, $C_1$–$C_4$ haloalkyl, methylenedioxydiyl, ethylenedioxydiyl; ($C_1$–$C_{10}$ alkoxy) carbonyl; aryl($C_1$–$C_{10}$ alkoxy)carbonyl where the aryl group is optionally substituted with 0–3 groups selected from hydroxy, halogen, $C_1$–$C_6$ alkoxy, $C_1$–$C_6$ alkyl, $CF_3$, $S(O)_mCH_3$, $-N(CH_3)_2$, $C_1$–$C_4$ haloalkyl, methylenedioxydiyl, ethylenedioxydiyl; or heteroaryl ($C_1$–$C_5$)alkyl where the heteroaryl group is optionally substituted with 0–2 groups selected from hydroxy, halogen, $C_1$–$C_6$ alkoxy, $C_1$–$C_6$ alkyl, $CF_3$, $S(O)_mCH_3$, $-N(CH_3)_2$, $C_1$–$C_4$ haloalkyl, methylenedioxydiyl, ethylenedioxydiyl;

$R^{2a}$ is $R^2$ or $R^2(R^3)N(R^2N=)C$;

U is a single bond,

V is selected from:
- a single bond;
- -($C_1$–$C_7$ alkyl)-, substituted with 0–3 groups independently selected from $R^6$ or $R^7$;
- -($C_2$–$C_7$ alkenyl)-, substituted with 0–3 groups independently selected from $R^6$ or $R^7$;
- -($C_2$–$C_7$ alkynyl)-, substituted with 0–3 groups independently selected from $R^6$ or $R^7$;
- -(phenyl)-Q-, said phenyl substituted with 0–2 groups independently selected from $R^6$ or $R^7$;
- -(pyridyl)-Q-, said pyridyl substituted with 0–2 groups independently selected from $R^6$ or $R^7$; or
- -(pyridazinyl)-Q-, said pyridazinyl substituted with 0–2 groups independently selected from $R^6$ or $R^7$, Q is selected from
- a single bond,
- —O—, —S(O)$_m$—, —N($R^{12}$)—, —(CH$_2$)m—, —C(=O)—, —N($R^{5a}$)C(=O)—, —C(=O)N($R^{5a}$)—, —CH$_2$O—, —OCH$_2$—, —CH$_2$N($R^{12}$)—, —N($R^{12}$)CH$_2$—, —CH$_2$C(=O)—, —C(=O)CH$_2$—, —CH$_2$S(O)$_m$—, or —S(O)$_m$CH$_2$—,
- provided that when b is a single bond, and $R^1$—U—V— is a substituent on C5 of the central 5-membered ring of Formula Ic, then Q is not —O—, —S(O)$_m$—, —N($R^{12}$)—, —C(=O)N($R^{5a}$)—, —CH$_2$O—, CH$_2$N($R^{12}$)— or —CH$_2$S(O)$_m$—;

W is selected from:
- —(C($R^4$)$_2$)—C(=O)—N($R^{5a}$)—, or
- —C(=O)—N($R^{5a}$)—(C($R^4$)$_2$)—;

X is —C($R^4$)($R^8$)—CHR$^{4a}$—;

$R^4$ is selected from H, $C_1$–$C_{10}$ alkyl, $C_1$–$C_{10}$ alkylcarbonyl, aryl, arylalkyl, cycloalkyl, or cycloalkylalkyl;

$R^{4a}$ is selected from hydroxy, $C_1$–$C_{10}$ alkoxy, nitro, —N($R^5$)$R^{5a}$, —N($R^{12}$)$R^{13}$, or —N($R^{16}$)$R^{17}$, aryl substituted with 0–3 $R^6$, or ($C_1$–$C_{10}$ alkyl)carbonyl;

$R^{4b}$ is selected from H, $C_1$–$C_6$ alkyl, $C_2$–$C_6$ alkenyl, $C_2$–$C_6$ alkynyl, hydroxy, $C_1$–$C_6$ alkoxy, $C_1$–$C_6$ alkylthio, $C_1$–$C_6$ alkylsulfinyl, $C_1$–$C_6$ alkylsulfonyl, nitro, ($C_1$–$C_6$ alkyl)carbonyl, $C_6$–$C_{10}$ aryl, —N($R^{12}$)$R^{13}$, halo, CF$_3$, CN, ($C_1$–$C_6$ alkoxy)carbonyl, carboxy, piperidinyl, morpholinyl or pyridyl;

$R^5$ is selected from H or $C_1$–$C_{10}$ alkyl substituted with 0–6 $R^{4b}$;

$R^{5a}$ is selected from hydrogen, hydroxy, $C_1$ to $C_8$ alkyl, $C_2$ to $C_6$ alkenyl, $C_3$ to $C_{11}$ cycloalkyl, $C_4$ to $C_{11}$ cycloalkylmethyl, $C_1$–$C_6$ alkoxy, benzyloxy, $C_6$ to $C_{10}$ aryl, heteroaryl, heteroarylalkyl, $C_7$ to $C_{11}$ arylalkyl, or adamantylmethyl, $C_1$–$C_{10}$ alkyl substituted with 0–2 $R^{4b}$;

alternately, $R^5$ and $R^{5a}$ can be taken together to be 3-azabicyclononyl, 1,2,3,4-tetrahydro-1-quinolinyl, 1,2,3,4-tetrahydro-2-isoquinolinyl, 1-piperidinyl, 1-morpholinyl, 1-pyrrolidinyl, thiamorpholinyl, thiazolidinyl or 1-piperazinyl, each being optionally substituted with $C_1$–$C_6$ alkyl, $C_6$–$C_{10}$ aryl, heteroaryl, $C_7$–$C_{11}$ arylalkyl, ($C_1$–$C_6$ alkyl)carbonyl, ($C_3$–$C_7$ cycloalkyl)carbonyl, ($C_1$–$C_6$ alkoxy)carbonyl or ($C_7$–$C_{11}$ arylalkoxy) carbonyl;

$R^{5b}$ is selected from $C_1$–$C_8$ alkyl, $C_2$–$C_6$ alkenyl, $C_3$–$C_{11}$ cycloalkyl, $C_4$–$C_{11}$ cycloalkylmethyl, $C_6$—$C_{10}$ aryl, $C_7$–$C_{11}$ arylalkyl, or $C_1$–$C_{10}$ alkyl substituted with 0–2 $R^{4b}$ Y is selected from hydroxy, $C_1$ to $C_{10}$ alkyloxy, $C_3$ to $C_{11}$ cycloalkyloxy, $C_6$ to $C_{10}$ aryloxy, $C_7$ to $C_{11}$ aralkyloxy, $C_3$ to $C_{10}$ alkylcarbonyloxyalkyloxy, $C_3$ to $C_{10}$ alkoxycarbonyloxyalkyloxy, $C_2$ to $C_{10}$ alkoxycarbonylalkyloxy, $C_5$ to $C_{10}$ cycloalkylcarbonyloxyalkyloxy, $C_5$ to $C_{10}$ cycloalkoxycarbonyloxyalkyloxy, $C_5$ to $C_{10}$ cycloalkoxycarbonylalkyloxy, $C_7$ to $C_{11}$ aryloxycarbonylalkyloxy, $C_8$ to $C_{12}$ aryloxycarbonyloxyalkyloxy, $C_8$ to $C_{12}$ arylcarbonyloxyalkyloxy, $C_5$ to $C_{10}$ alkoxyalkylcarbonyloxyalkyloxy, $C_5$ to $C_{10}$ (5-alkyl-1,3-dioxa-cyclopenten-2-one-yl)methyloxy, or $C_{10}$ to $C_{14}$ (5-aryl-1,3-dioxa-cyclopenten-2-one-yl)methyloxy;

$R^6$ and $R^7$ are each independently selected from H, $C_1$–$C_{10}$ alkyl, hydroxy, $C_1$–$C_{10}$ alkoxy, nitro, ($C_1$–$C_{10}$ alkyl)carbonyl, —N($R^{12}$)$R^{13}$, cyano, or halo;

$R^{12}$ and $R^{13}$ are each independently selected from H, $C_1$–$C_{10}$ alkyl, ($C_1$–$C_{10}$ alkoxy)carbonyl, ($C_1$–$C_{10}$ alkyl)carbonyl, $C_1$–$C_{10}$ alkylsulfonyl, aryl($C_1$–$C_{10}$ alkyl)sulfonyl, arylsulfonyl, heteroarylsulfonyl, heteroarylcarbonyl, heteroarylalkylcarbonyl or aryl, wherein said aryl groups being optionally substituted with 0–3 substituents selected from the group consisting of: $C_1$–$C_4$ alkyl, $C_1$–$C_4$ alkoxy, halo, CF$_3$, and NO$_2$;

$R^{15}$ is selected from H, $C_1$–$C_{10}$ alkyl, $C_2$–$C_{10}$ alkenyl, $C_2$–$C_{10}$ alkynyl, $C_1$–$C_{10}$ alkoxy, aryl, heteroaryl or ($C_1$–$C_{10}$ alkoxy)carbonyl, CO$_2$R$^5$ or —C(=O)N($R^5$)$R^{5a}$;

$R^{16}$ is selected from:
- —C(=O)—O—$R^{18a}$,
- —C(=O)—$R^{18b}$,
- —C(=O)N($R^{18b}$)$_2$,
- —SO$_2$—$R^{18a}$, or
- —SO$_2$—N($R^{18b}$)$_2$;

$R^{17}$ is selected from: H or $C_1$–$C_5$ alkyl;

$R^{18a}$ is selected from:
- $C_1$–$C_8$ alkyl substituted with 0–2 $R^{19}$,
- $C_2$–$C_9$ alkenyl substituted with 0–2 $R^{19}$,
- $C_2$–$C_8$ alkynyl substituted with 0–2 $R^{19}$,
- $C_3$–$C_8$ cycloalkyl substituted with 0–2 $R^{19}$,
- aryl substituted with 0–4 $R^{19}$,
- aryl($C_1$–$C_6$ alkyl)-substituted with 0–4 $R^{19}$,
- a heterocyclic ring system selected from pyridinyl, furanyl, thiazolyl, thienyl, pyrrolyl, pyrazolyl, triazolyl, imidazolyl, benzofuranyl, indolyl, indolinyl, quinolinyl, isoquinolinyl, isoxazolyl, isoxazolinyl, benzimidazolyl, piperidinyl, tetrahydrofuranyl, pyranyl, pyrimidinyl, 3H-indolyl, pyrrolidinyl, piperidinyl, indolinyl, or morpholinyl, said heterocyclic ring being substituted with 0–4 $R^{19}$;
- $C_1$–$C_6$ alkyl substituted with a heterocyclic ring system selected from pyridinyl, furanyl, thiazolyl, thienyl, pyrrolyl, pyrazolyl, imidazolyl, isoxazolyl, isoxazolinyl, benzofuranyl, indolyl, indolenyl, quinolinyl, isoquinolinyl, benzimidazolyl, piperidinyl, tetrahydrofuranyl, pyranyl, pyridinyl, 3H-indolyl, indolyl, pyrrolidinyl, piperidinyl, indolinyl, or morpholinyl, said heterocyclic ring being substituted with 0–4 $R^{19}$;

$R^{18b}$ is selected from $R^{18}$a or H;

$R^{19}$ is selected from H, halogen, CF$_3$, CN, NO$_2$, NR$^{12}$R$^{13}$, $C_1$–$C_8$ alkyl, $C_2$–$C_6$ alkenyl, $C_2$–$C_6$ alkynyl, $C_1$–$C_6$ alkoxy, $C_3$–$C_{11}$ cycloalkyl, $C_4$–$C_{11}$ cycloalkylalkyl, aryl, heteroaryl, aryl($C_1$–$C_6$ alkyl)-, ($C_1$–$C_4$ alkyl)sulfonyl, aryl-sulfonyl, or $C_1$–$C_4$ alkoxycarbonyl;

n is 0–4;

p' is 1–7;

p" is 1–7;
r is 0–3.
More preferred compounds have the formula:

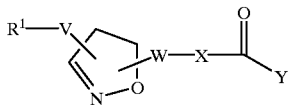
(Ib)

or a pharmaceutically acceptable salt thereof,
wherein:
$R^1$ is selected from: $R^{2a}(R^3)N-$, $R^2NH(R^2N=)C-$, $R^2NH(R^2N=)CNH-$, $R^{2a}(R^3)N(CH_2)_{p'}Z-$, $R^2NH(R^2N=)C(CH_2)_{p''}Z-$, $R^2(R^3)NC(O)-$, $R^2(R^5O)N(R^2N=)C-$, $R^2(R^3)N(R^5ON=)C-$;

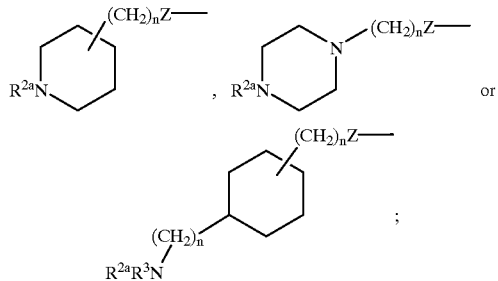

n is 0–1;
p' is 4–6;
p" is 2–4;
Z is selected from a bond or O;
V is a single bond, -(phenyl)- or -(pyridyl)-;
W is selected from:
 $-(C(R^4)_2)-C(=O)-N(R^{5a})-$,
 $-C(=O)-N(R^{5a})-CH_2-$;
X is selected from:
 $-CH_2-CH(N(R^{16})R^{17})-$, or
 $-CH_2-CH(NR^5R^{5a})-$;
Y is selected from:
 hydroxy;
 $C_1$ to $C_{10}$ alkoxy;
 methylcarbonyloxymethoxy-;
 ethylcarbonyloxymethoxy-;
 t-butylcarbonyloxymethoxy-;
 cyclohexylcarbonyloxymethoxy-;
 1-(methylcarbonyloxy)ethoxy-;
 1-(ethylcarbonyloxy)ethoxy-;
 1-(t-butylcarbonyloxy)ethoxy-;
 1-(cyclohexylcarbonyloxy)ethoxy-;
 i-propyloxycarbonyloxymethoxy-;
 t-butyloxycarbonyloxymethoxy-;
 1-(i-propyloxycarbonytoxy)ethoxy-;
 1-(cyclohexyloxycarbonyloxy)ethoxy-;
 1-(t-butyloxycarbonyloxy)ethoxy-;
 dimethylaminoethoxy-;
 diethylaminoethoxy-;
 (5-methyl-1,3-dioxacyclopenten-2-on-4-yl)methoxy-;
 (5-(t-butyl)-1,3-dioxacyclopenten-2-on-4-yl)methoxy-;
 (1,3-dioxa-5-phenyl-cyclopenten-2-on-4-yl)methoxy-;
 1-(2-(2-methoxypropyl)carbonyloxy)ethoxy-;

$R^{16}$ is selected from:
 $-C(=O)-O-R^{18a}$,
 $C(=O)-R^{18b}$,
 $-S(=O)_2-R^{18a}$ or
 $-SO_2-N(R^{18b})_2$;
$R^{17}$ is selected from H or $C_1-C_5$ alkyl;
$R^{18a}$ is selected from:
 $C_1-C_8$ alkyl substituted with 0–2 $R^{19}$,
 $C_2-C_8$ alkenyl substituted with 0–2 $R^{19}$,
 $C_2-C_8$ alkynyl substituted with 0–2 $R^{19}$,
 $C_3-C_8$ cycloalkyl substituted with 0–2 $R^{19}$,
 aryl substituted with 0–4 $R^{19}$,
 aryl($C_1-C_6$ alkyl)-substituted with 0–4 $R^{19}$,
 a heterocyclic ring system selected from pyridinyl, furanyl, thiazolyl, thienyl, pyrrolyl, pyrazolyl, triazolyl, imidazolyl, benzofuranyl, indolyl, indolinyl, quinolinyl, isoquinolinyl, isoxazolyl, isoxazolinyl, benzimidazolyl, piperidinyl, tetrahydrofuranyl, pyranyl, pyrimidinyl, 3H-indolyl, pyrrolidinyl, piperidinyl, indolinyl, or morpholinyl, said heterocyclic ring being substituted with 0–4 $R^{19}$;
 $C_1-C_6$ alkyl substituted with a heterocyclic ring system, selected from pyridinyl, furanyl, thiazolyl, thienyl, pyrrolyl, pyrazolyl, imidazolyl, isoxazolyl, isoxazolinyl, benzofuranyl, indolyl, indolenyl, quinolinyl, isoquinolinyl, benzimidazolyl, piperidinyl, tetrahydrofuranyl, pyranyl, pyridinyl, 3H-indolyl, indolyl, pyrrolidinyl, piperidinyl, indolinyl, or morpholinyl, said heterocyclic ring being substituted with 0–4 $R^{19}$.

A specifically preferred compound has the formula:

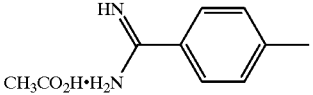

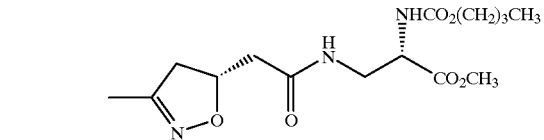

Other salts of this compound are also specifically preferred.
Specific examples of other compounds useful in this invention are xemilofiban, orbofiban, lamifiban, paranyline, pentamidine, and factor Xa compounds from DuPont Merck which have an amidine group. This list of compounds is not meant to be exhaustive of those useful in the present invention. Generally, the concentration of the active pharmaceutical compound in the formulation is in the range of 0.05–25 weight percent of the composition. In most preferred embodiments, the concentration of the active pharmaceutical compound is in the range of 0.3–2 weight percent.

Compounds containing ester and amidine functional groups are susceptible to pH dependent hydrolytic reactions. The environment of the functional groups can be altered by the addition of a pH modifying agent. The saturated solution pH of this agent should be about the same as the pH of maximum stability of the compound being formulated. Examples of these agents include, but not limited to, organic acids such as citric acid, monosodium citrate, monobasic sodium phosphate, disodium citrate, lactic acid, fumaric acid, malic acid, benzoic acid, tartaric acid, and ascorbic acid (or their acidic salts when applicable); and inorganic acids such as hydrochloric acid. Mixtures of these ingredients or mixtures of other substances (such as sodium citrate and citric acid) that yields these ingredients may also be used. Disodium citrate is preferred, particularly for use with the above specifically preferred compound.

The amount of pH modifying agent used is sufficient to modify the pH of formulation composition to substantially that of the active pharmaceutical compound in the formulation as measured at pH of maximum stability. Determination of pH of maximum stability is known to those skilled in the art. Typically, at least 2 mmole % of pH modifying agent is used based on the components in the composition. In general there is no need to use more than 20 mmole percent of pH modifying agent. In most preferred embodiments, the pH modifying agent will make up about 1–3 weight percent of the composition, preferably about 1.25–2.5 weight percent.

The formulation of this invention can be prepared by a variety of processes and order of addition of reagents. It is required that water is added during the preparation of the dosage form, either as water per se, or as an aqueous solution containing any of the excipients such as the pH modifying agent. The formulation can be prepared in the following manner. The pharmaceutical compound can be blended and/or milled with some or all of the other ingredients, including the pH modifying agent. Some water, possibly containing the pH modifying agent, is added to produce a slightly cohesive mass such as in the well-known wet granulation process. The pH modifying agent can be added either in solution or in solid form. This mass can be dried and milled, and additional ingredients can also be added if desired. The resulting blend can be encapsulated or tableted. If desired, these dosage forms can then be coated as known to those skilled in the art. The pharmaceutical compound does not have to be added before the addition of water. The formulation can also be prepared in the following manner: Water can be added to a mixture of some or all of the inactive ingredients including the pH modifying agent. The pH modifying agent can be added either in a solution or dry form. The resulting mass can be dried and milled if desired. The pharmaceutical compound and any additional ingredients can be added after drying.

The present invention will be illustrated by following examples. The examples are for illustration only; they do not necessarily represent optimized formulations or processes. The examples refer to the use of Compound (I) as the pharmaceutical compound. This compound has the following structural formula:

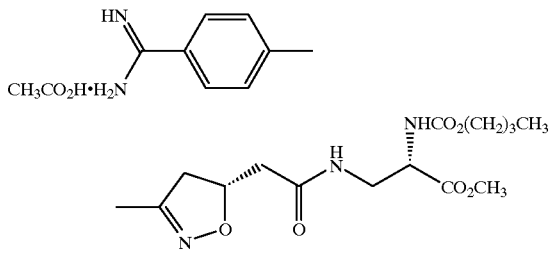

The pH of maximum stability is about 4. The pH of maximum stability is determined by preparing solutions of the compound at different pH values and observing and measuring degradation over time.

EXAMPLES

In the following examples the glycoprotein IIb/IIa receptor antagonist, Compound (I) is used as a model drug. It has a carboxylic acid methyl ester and a benzamidine group that undergo hydrolysis in the solid state in the presence of excipients. The utility of the invention is demonstrated by the improved stability of Compound (I) capsules and tablets. In these examples, stability of capsules and tablets was evaluated as follows:

Capsules and tablets were packaged into high density polyethylene (HDPE) bottles in counts of 10 or 6, respectively, with 0.6 gm silica gel desiccant. The packaged HDPE bottles were stored in stability chambers at 40° C/75% RH, 30° C/60% RH or 25° C/60% RH. Samples were taken at different time intervals and the contents were analyzed for degradation products by high pressure liquid chromatography (HPLC). An HPLC system equipped with automatic sampler, heated column compartment, gradient elution pump, and variable wavelength UV detector set at 280 nm (Model 1050/Hewlett Packard) was used for analysis of the capsule and tablet samples. A Waters Symmetry column was used with gradient elution of the mobile phase from 10:90 to 60:40 acetonitrile (ACN)/0.05 wt. % trifluoracetic acid (TFA) in water over 30 minutes at a flow rate of 1.5 mL/min and a column temperature of 35° C.

| Control Tablets and capsules were prepared from the following formulation by a dry granulation process. | |
| --- | --- |
| Ingredient | mg/capsule or tablet |
| Compound (I) | 0.23 |
| Anhydrous lactose | 57.67 |
| Disodium citrate | 1.50 |
| Magnesium stearate | 0.60 |
| Total | 60 |

Disodium citrate was pre-mixed with a portion of anhydrous lactose using a Turbula® T2C mixer (Willy A. Bachofen AG, Basel, Switzerland). Compound (I) was then triturated with the anhydrous lactose/disodium citrate pre-blend in a mortar and pestle using a geometric dilution technique. The resulting blend, which contains Compound (I), disodium citrate and anhydrous lactose, was then mixed with the remaining portion of anhydrous lactose and 0.75 wt. % of magnesium stearate using a V-blender (Patterson-Kelley, East Strosburg, Pa.). The discharged blend from the V-blender was compressed into tablets (slugs) to a target weight of 200 mg and a target hardness of 4 SCAU on a Stokes® single station press (Pennwalt Corporation, Warminster, Pa.) using 11/32 inch (0.87 cm) standard concave tooling. The slugs were hand screened through a 25 mesh screen and the resulting granulation was blended with 0.25 wt. % of magnesium stearate in the V-blender. The granulation, 60 mg, was filled into size 3 hard gelatin capsules on a Zanasi® AZ5 capsule filling machine, or compressed into tablets of 60 mg weight on the Stokes® single station press using 7/32 inch (0.56 cm) standard concave tooling.

Example 1
Tablets and capsules were prepared from the following formulation by a wet granulation process.

| Ingredient | mg/capsule or tablet |
| --- | --- |
| Compound (I) | 0.23 |
| Anhydrous lactose | 56.47 |
| Povidone (binder) | 1.20 |
| Disodium citrate | 1.50 |
| Magnesium stearate | 0.60 |
| Total | 60 |

Compound (I) was triturated with a portion of of anhydrous lactose in a mortar and pestle using a geometric dilution technique. The resulting Compound (I)/anhydrous lactose pre-blend was mixed with the remaining amount of anhydrous lactose in the 5 liter bowl of the Key® KG-5 high shear granulator (Key International, Englishtown, N.J.). The blend was then granulated with an aqueous granulating solution consisting of disodium citrate and povidone in an amount of purified water representing 9.3 wt. % of total solids in the formulation. The granulating solution was adjusted to pH 4 with 1N hydrochloric acid. The wet granulation was screened through 8 mesh screen and dried in a vacuum oven at 40° C. to a moisture content of 0.7 wt. %. The dried granulation was screened through a 25 mesh screen and blended with magnesium stearate in a V-blender. The granulation, 60 mg, was filled into size three hard gelatin capsules on the Zanasi® AZ5 capsule filling machine, or compressed into 60 mg tablets on the Stokes® single station press using 7/32 inch (0.56 cm) standard concave tooling.

Example 2
Tablets and capsules were prepared from the following formulation by a wet granulation process.

| Ingredient | mg/capsule or tablet |
| --- | --- |
| Compound (I) | 0.23 |
| Anhydrous lactose | 53.77 |
| Crospovidone (disintegrant) | 2.70 |
| Povidone (binder) | 1.20 |
| Disodium citrate | 1.50 |
| Magnesium stearate | 0.60 |
| Total | 60 |

Compound (I) was triturated with a portion of of anhydrous lactose in a mortar and pestle using a geometric dilution technique. The resulting Compound (I)/anhydrous lactose pre-blend was mixed with the remaining amount of anhydrous lactose and 2/3 the quantity of crospovidone in the 5 liter bowl of the Key® KG-5 high shear granulator. The blend was then granulated with an aqueous granulating solution consisting of disodium citrate and povidone in an amount of purified water representing 9.3 wt. % of total solids in the formulation. The granulating solution was adjusted to pH 4 with 1N hydrochloric acid. The wet granulation was screened through 8 mesh screen and dried in a vacuum oven at 40° C. to a moisture content of 0.7 wt. %. The dried granulation was screened through a 25 mesh screen. The screened granulation was blended with the remaining amount of crospovidone and magnesium stearate in a V-blender. The granulation, 60 mg, was filled into size three hard gelatin capsules on the Zanasi® AZ5 capsule filling machine, or compressed into 60 mg tablets on the Stokes® single station press using 7/32 inch (0.56 cm) standard concave tooling.

Example 3
Capsules were manufactured from the following formulation by a wet granulation process.

| Ingredient | mg/capsule |
| --- | --- |
| Compound (I) | 0.23 |
| Anhydrous lactose | 56.47 |
| Povidone | 1.20 |
| Monosodium citrate | 1.50 |
| Magnesium stearate | 0.60 |
| Total | 60 |

Compound (I) was triturated with a portion of anhydrous lactose in a mortar and pestle using a geometric dilution technique. The resulting Compound (I)/anhydrous lactose pre-blend was mixed with the remaining portion of anhydrous lactose and monosodium citrate in the 5 liter bowl of the Key® KG-5 high shear granulator. The blend was then granulated with an aqueous granulating solution consisting of povidone in an amount of purified water representing 9.3 wt. % of total solids in the formulation. The wet granulation was screened through 8 mesh screen and dried in a vacuum oven at 40° C. to a moisture content of 0.7 wt. %. The dried granulation was screened through a 25 mesh screen and blended with magnesium stearate in a V-blender. The granulation, 60 mg, was filled into size three hard gelatin capsules on the Zanasi® AZS capsule filling machine.

Example 4
Tablets were manufactured from the following formulation by a wet granulation process.

| Ingredient | mg/tablet |
| --- | --- |
| Compound (T) | 0.23 |
| Anhydrous lactose | 57.22 |
| Povidone | 1.20 |
| Disodium citrate | 0.75 |
| Magnesium stearate | 0.60 |
| Total | 60 |

Compound (I) was triturated with a portion of anhydrous lactose in a mortar and pestle using a geometric dilution technique. The resulting Compound (I)/anhydrous lactose pre-blend was mixed with the remaining portion of anhydrous lactose in the 5 liter bowl of the Key® KG-5 high shear granulator. The blend was then granulated with an aqueous granulating solution consisting of disodium citrate and povidone in an amount of purified water representing 9.3 wt. % of total solids in the formulation; the granulating solution adjusted to pH 4 with 1N hydrochloric acid. The wet granulation was screened through 8 mesh screen and dried in a vacuum oven at 40° C. to a moisture content of 0.7%. The dried granulation was screened through a 25 mesh screen and blended with magnesium stearate in a V-blender. The granulation was compressed into 60 mg tablets on the Stokes® single station press using 7/32 inch (0.56 cm) standard concave tooling.

Example 5
Tablets were manufactured from the following
formulation by a wet granulation process.

| Ingredient | mg/tablet |
| --- | --- |
| Compound (I) | 0.23 |
| Anhydrous lactose | 56.58 |
| Povidone | 1.20 |
| Sodium citrate (dihydrate) | 0.55 |
| Citric acid (anhydrous) | 0.84 |
| Magnesium stearate | 0.60 |
| Total | 60 |

Compound (I) was triturated with a portion of anhydrous lactose in a mortar and pestle using a geometric dilution technique. The resulting Compound (I)/anhydrous lactose pre-blend was mixed with the remaining portion of anhydrous lactose in the 5 liter bowl of the Key® KG-5 high shear granulator. The blend was then granulated with an aqueous granulating solution consisting of (tri)sodium citrate, citric acid, povidone in an amount of purified water representing 9.3 wt. % of the total solids in the formulation. The wet granulation was screened through 8 mesh screen and dried in a vacuum oven at 40° C. to a moisture content of 0.7 wt. %. The dried granulation was screened through a 25 mesh screen and blended with magnesium stearate in a V-blender. The granulation was compressed into 60 mg tablets on the Stokes® single station press using 7/32 inch (0.56 cm) standard concave tooling.

Example 6
Film-coated tablets were manufactured from
the following formulation by a wet granulation process.

| Ingredient | mg/tablet |
| --- | --- |
| Core tablet | |
| Compound (T) | 0.58 |
| Anhydrous lactose | 55.03 |
| Povidone | 1.20 |
| Crospovidone | 1.20 |
| Sodium citrate (dihydrate) | 0.55 |
| Citric acid (anhydrous) | 0.84 |
| Magnesium stearate | 0.60 |
| Film coat | |
| Opadry ® II white* | 1.80 |
| Total | 61.80 |

*Trademark of Colorcon for its powder concentrate for film forming containing a polymer, plasticizer and pigment Compound (I) was triturated with a portion of anhydrous lactose in a mortar and pestle using a geometric dilution technique. The resulting Compound (I)/anhydrous lactose pre-blend was mixed with the remaining amount of anhydrous lactose and ½ the quantity of crospovidone in the 5 liter bowl of the Key® KG-5 high shear granulator. The blend was then granulated with an aqueous granulating solution consisting of (tri)sodium citrate, citric acid, povidone in an amount of purified water representing 9.3 wt. % of the total solids in the formulation. The wet granulation was milled through a screen with opening diameter of 0.094 inch (0.24 cm) using a Quadro Comil® 197S. The granulation was dried in an Aeromatic® STREA-1 fluid bed at inlet air temperature of 60° C. to a moisture content of not more than (NMT) 0.8 wt. %. The dried granulation was milled through a screen with opening diameter of 0.032 inch (0.08 cm) using the Quadro Comil® 197S. The milled granulation was blended with the remaining quantity of crospovidone and magnesium stearate in a V-blender. The granulation was compressed into 60 mg tablets on the Stokes® single station press using 7/32 inch (0.56 cm) standard concave tooling. A coating suspension was prepeared by dispersing Opadry II in purified water at 20 wt. % concentration using a Lightnin® mixer. The resulting suspension was applied to a 3 wt. % weight gain to core tablets in a Vector HCT-30 Hi-Coater® (30-cm pan).

Example 7
Tablets were manufactured from the following
formulation by a wet granulation process.

| Ingredient | mg/tablet |
| --- | --- |
| Compound (I) | 1.17 |
| Anhydrous lactose | 55.53 |
| Povidome | 1.20 |
| Disodium citrate | 1.50 |
| Magnesium stearate | 0.60 |
| Total | 60 |

Compound () was triturated with a portion of anhydrous lactose in a mortar and pestle using a geometric dilution technique. The resulting Compound (I)/anhydrous lactose pre-blend was mixed with the remaining amount of anhydrous lactose in the 5 liter bowl of the Key® KG-5 high shear granulator. The blend was then granulated with an aqueous granulating solution consisting of disodium citrate and povidone in an amount of purified water representing 9.3 wt. % of total solids in the formulation. The granulating solution was adjusted to pH 4 with 1N hydrochloric acid. The wet granulation was screened through 8 mesh screen and dried in a vacuum oven at 40° C. to a moisture content of 0.7 wt. %. The dried granulation was screened through a 25 mesh screen and blended with magnesium stearate in a V-blender. The granulation was compressed into 60 mg tablets on the Stokes® single station press using 7/32 inch (0.56 cm) standard concave tooling.

EXAMPLE 8

Compound (I) bilayer tablets consisting of one active layer and one placebo layer were prepared using a Carver® press. Total tablet weight was 120 mg, 60 mg active layer and 60 mg placebo layer. The active layer was compressed from granulation of similar composition and manufacturing process to Example 7. The placebo layer was compressed form a blend prepared by mixing anhydrous lactose with 1 wt. % magnesium stearate using the Turbula® mixer. The placebo blend, 60 mg, was compressed to form the first layer using 9/32 inch (0.71 cm) standard concave tooling. The active granulation, 60 mg, was then added to the die cavity containing the placebo layer and the second layer was compressed.

Example 9
Tablets were manufactured from the following formulation
by a wet granulation process.

| Ingredient | mg/tablet |
| --- | --- |
| Compound (I) | 0.23 |
| Anhydrous lactose | 56.47 |
| Povidone | 1.20 |
| Disodium citrate | 1.50 |
| Magnesium stearate | 0.60 |
| Total | 60 |

Compound (I) was triturated with a portion of anhydrous lactose in a mortar and pestle using a geometric dilution technique. The resulting Compound (I)/anhydrous lactose pre-blend was mixed with the remaining portion of anhydrous lactose in the 5 liter bowl of the Key® KG-5 high shear granulator. The blend was then granulated with an aqueous granulating solution consisting of disodium citrate and povidone in an amount of purified water representing 9.3 wt. % of total solids in the formulation. The granulating solution was adjusted to pH 4 with 1N hydrochloric acid. The wet granulation was screened through 8 mesh screen and dried in an Aeromatic® STREA-1 fluid bed at inlet air temperature of 60° C. to a moisture content of 0.7 wt. %. The dried granulation was milled through a screen with opening diameter of 0.032 inch (0.08 cm) using a Quadro Comil® 197S, and was then blended with magnesium stearate in a V-blender. The granulation was compressed into 60 mg tablets on the Stokes® single station press using 7/32 inch (0.56 cm) standard concave tooling.

Example 10
Tablets were manufactured from the following
formulation by a wet granulation process.

| Ingredient | mg/tablet |
| --- | --- |
| Compound (I) | 0.23 |
| Anhydrous lactose | 56.47 |
| Povidone | 1.20 |
| Disodium citrate | 1.50 |
| Magnesium stearate | 0.60 |
| Total | 60 |

Anhydrous lactose was granulated in the 5 liter bowl of the Key® KG-5 high shear granulator with an aqueous granulating solution consisting of disodium citrate and povidone in an amount of purified water representing 9.3 wt. % of total solids in the formulation, and which was adjusted to pH 4 with 1N hydrochloric acid. The wet granulation was screened through 8 mesh screen and dried in a vacuum oven at 40° C. to a moisture content of 0.7 wt. %, and the dried granulation was screened through a 25 mesh screen. Compound (I) was triturated with a portion of milled granulation in a mortar and pestle using a geometric dilution technique. The resulting mix was then blended with the remaining quantity of the milled granulation and magnesium stearate in a V-blender. The granulation was compressed into 60 mg tablets on the Stokes® single station press using 7/32 inch (0.56 cm) standard concave tooling.

The stability results are shown in Table 1. From the Table it can be seen that the addition of a pH modifying agent during formulation manufacture which uses water improves hydrolytic stability of Compound (I) in its formulation compared to the use of a pH modifying agent in a dry manufacturing process. Such results are not expected.

Example 11
Tablets were manufactured from the following
formulation by the wet granulation process.

| Ingredient | mg/tablet |
| --- | --- |
| Compound (I) | 0.235 |
| Anhydrous lactose | 57.67 |
| Disodium citrate | 1.5 |
| Magnesium stearate | 0.6 |
| Total | 60 |

Compound (I) was triturated with a portion of anhydrous lactose in a mortar and pestle using a geometric dilution technique. The resulting Compound (I)/anhydrous lactose preblend was mixed with the remaining portion of anhydrous lactose in the 5 liter bowl of the Key® KG-5 high shear granulator. The blend was then granulated with an aqueous granulating solution consisting of disodium citrate in amount of purified water representing 9.3 wt. % of total solids in the formulation; granulating solution adjusted to pH 4 with 1N hydrochloric acid. The wet granulation was screened through 8 mesh screen and dried in a vacuum oven at 40 degrees celcius to a moisture content of 0.7%. The dried granulation was screened through a 25 mesh screen and blended with magnesium stearate in a V-blender. The granulation was compressed into 60 mg tablets on the Stokes® single station press using 7/32 inch (0.56 cm) standard concave tooling.

TABLE 1

| Storage Condition/ | WT. % DEGRADANT | | | | | | |
| --- | --- | --- | --- | --- | --- | --- | --- |
| | Control | | Example 1 | | Example 2 | | Example 3 |
| Timepoint | Capsules | Tablets | Capsules | Tablets | Capsules | Tablets | Capsules |
| 40° C./75% RH | | | | | | | |
| a | | | | | | | |
| Time zero | 0.15 | 0.55 | 0.10 | 0.17 | 0.17 | 0.18 | 0.19 |
| 1 mo | 0.79[c] | 1.17 | 0.26[c] | 0.23 | 0.35 | 0.27 | 0.41 |
| 2 mo | 2.41 | 2.06 | 0.87 | 0.37 | 0.54 | 0.43 | 0.68 |

TABLE 1-continued

|  |  |  |  |  |  |  |  |
|---|---|---|---|---|---|---|---|
| 3 mo | 3.41 | 3.44 | 1.72 | 0.59 | 0.96 | 0.56 | 1.17 |
| 6 mo | 7.98 | ND | 4.75 | 2.47 | 2.38 | 2.11 | ND |
| b |  |  |  |  |  |  |  |
| Time zero | 0.15 | 0.23 | 0.13 | 0.14 | 0.14 | 0.15 | 0.15 |
| 1 mo | 0.44[c] | 0.75 | 0.19[c] | 0.21 | 0.23 | 0.19 | 0.42 |
| 2 mo | 1.01 | 1.36 | 0.36 | 0.29 | 0.32 | 0.26 | 0.58 |
| 3 mo | 1.22 | 2.18 | 0.51 | 0.37 | 0.44 | 0.34 | 0.82 |
| 6 mo | 2.09 | ND | 1.16 | 0.77 | 0.94 | 0.66 | ND |
| 30° C./60% RH |  |  |  |  |  |  |  |
| a |  |  |  |  |  |  |  |
| Time zero | 0.15 |  | 0.10 | 0.17 | 0.17 | 0.18 | 0.19 |
| 3 mo | 0.90 |  | 0.50 | 0.25[d] | 0.29 | 0.23 | 0.37 |
| 6 mo | 1.92 |  | 0.62 | 0.43[e] |  |  |  |
| 12 mo | 3.65 |  | 1.29 | 0.71 | ND | ND |  |
| b |  |  |  |  |  |  |  |
| Time zero | 0.15 |  | 0.13 | 0.14 | 0.14 | 0.15 | 0.15 |
| 3 mo | 0.43 |  | 0.20 | 0.23[d] | 0.21 | 0.19 | 0.33 |
| 6 mo | 0.77 |  | 0.26 | 0.30[e] |  |  |  |
| 12 mo | 1.24 |  | 0.41 | 0.36 | ND | ND |  |
| 25° C./60% RH |  |  |  |  |  |  |  |
| a |  |  |  |  |  |  |  |
| Time zero | 0.15 |  | 0.10 |  | 0.17 | 0.18 | 0.19 |
| 3 mo | 0.49 |  | 0.43 |  | 0.22 | 0.18 | 0.28 |
| 6 mo | 0.95 |  | 0.31 |  | 0.27 | 0.24 |  |
| 12 mo | 1.76 |  | 0.54 |  | ND | ND |  |
| b |  |  |  |  |  |  |  |
| Time zero | 0.15 |  | 0.13 |  | 0.14 | 0.15 | 0.15 |
| 3 mo | 0.28 |  | 0.19 |  | 0.17 | 0.17 | 0.24 |
| 6 mo | 0.45 |  | 0.19 |  | 0.22 | 0.18 |  |
| 12 mo | 0.71 |  | 0.24 |  | ND |  |  |

[a] = Ester hydrolysis product
[b] = Amidine hydrolysis product
[c] = 3 weeks time point
[d] = 4 months time point
[e] = 8 months time point
ND = not determined

| Storage Condition/ Timepoint | WT. % DEGRADANT | | | | | | | |
|---|---|---|---|---|---|---|---|---|
|  | Example 4 Tablets | Example 5 Tablets | Example 6 Tablets | Example 7 Tablets | Example 8 Tablets | Example 9 Tablets | Example 10 Tablets | Example 11 Tablets |
| 40° C./75% RH |  |  |  |  |  |  |  |  |
| a |  |  |  |  |  |  |  |  |
| Time zero | 0.14 | 0.15 | 0.13 | 0.11 | 0.19 | 0.21 | 0.15 | 0.16 |
| 1 mo | 0.20 | 0.21 | 0.16 | 0.20 | 0.17 | 0.30 | 0.20 | 0.20 |
| 2 mo | ND | 0.34 | ND | 0.20 |  | 0.48 | 0.27 | ND |
| 3 mo | 0.41 | 0.53 | 0.26 | 0.28 |  | 0.70 | 0.33 | 0.47 |
| 6 mo | 1.66 | 2.19 | 1.14 | 0.64 |  | 2.81 | 0.75 | ND |
| b |  |  |  |  |  |  |  |  |
| Time zero | 0.16 | 0.15 | 0.15 | 0.16 | 0.15 | 0.18 | 0.16 | 0.15 |
| 1 mo | 0.24 | 0.23 | 0.20 | 0.17 | 0.17 | 0.22 | 0.16 | 0.19 |
| 2 mo | ND | 0.35 | ND | 0.22 |  | 0.40 | 0.21 | ND |
| 3 mo | 0.43 | 0.45 | 0.29 | 0.25 |  | 0.41 | 0.25 | 0.27 |
| 6 mo | 0.85 | 0.86 | 0.54 | 0.38 |  | 0.86 | 0.42 | ND |
| 30° C./60% RH |  |  |  |  |  |  |  |  |
| a |  |  |  |  |  |  |  |  |
| Time zero |  |  |  | 0.11 |  |  |  | 0.16 |
| 3 mo |  |  |  | 0.16 |  |  |  | ND |
| 12 mo |  |  |  |  |  |  |  | 0.66 |
| b |  |  |  |  |  |  |  |  |
| Time zero |  |  |  | 0.16 |  |  |  | 0.16 |
| 3 mo |  |  |  | 0.19 |  |  |  | ND |
| 12 mo |  |  |  |  |  |  |  | 0.29 |

TABLE 1-continued

25° C./60% RH a

| | | | | | | | |
|---|---|---|---|---|---|---|---|
| Time zero | 0.14 | 0.15 | 0.13 | 0.11 | 0.21 | 0.15 | 0.16 |
| 3 mo | ND | 0.15[c] | 0.13 | 0.17 | 0.24[c] | 0.16[c] | ND |
| 6 mo | 0.18 | 0.20 | 0.15 | 0.16 | 0.26 | | ND |
| 12 mo | 0.27 | 0.34 | 0.20 | | 0.44 | | 0.29 | b

| | | | | | | | |
|---|---|---|---|---|---|---|---|
| Time zero | 0.16 | 0.15 | 0.15 | 0.16 | 0.18 | 0.16 | 0.15 |
| 3 mo | ND | 0.17[c] | 0.16 | 0.17 | 0.22[c] | 0.15[c] | ND |
| 6 mo | 0.23 | 0.24 | 0.18 | 0.17 | 0.23 | | ND |
| 12 mo | 0.27 | 0.29 | 0.22 | | 0.27 | | 0.21 |

[a] = Ester hydrolysis product
[b] = Amidine hydrolysis product
[c] = 2 months time point

What is claimed is:

1. A pharmaceutical composition comprising a tablet, capsule or other solid dosage form containing a pharmacologically effective amount of a pharmaceutical compound having the formula:

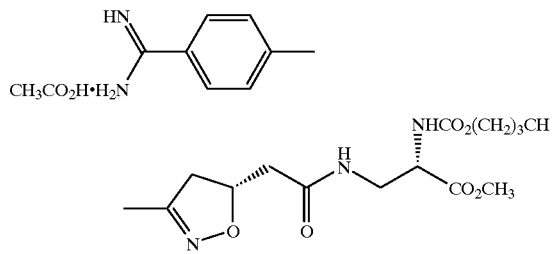

or a pharmaceutically acceptable salt thereof a pharmaceutically acceptable solid carrier, and a pharmaceutically acceptable organic acid in an amount effective to modify the pH of the composition to a pH of about 4.

2. A process for stabilizing a compound having the formula:

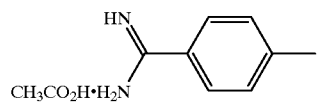
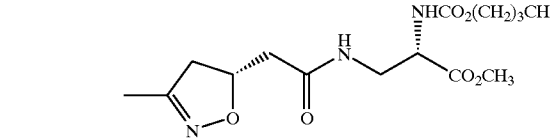

or a pharmaceutically acceptable salt thereof, against hydrolysis in a solid pharmaceutical formulation comprising: adding water during formulation manufacture and contacting the compound during formulation manufacture with a pharmaceutically acceptable acid having a pH in a saturated aqueous solution of about 4.

3. The process of claim 2 wherein the contacting and formulation manufacture is carried out in a wet granulation process.

* * * * *

UNITED STATES PATENT AND TRADEMARK OFFICE
CERTIFICATE OF CORRECTION

Page 1 of 2

PATENT NO. : 6,136,833

ISSUED : October 24, 2000

INVENTOR(S) : Sherif Ibrahim Farag Badawy, Donna Lynn Gilbert

It is certified that error appears in the above-identified patent and that said Letters Patent are hereby corrected as shown below:

At column 2, line 32, insert --(Ia)--

At column 6, lines 35-45; column 7, lines 48-58; column 17, lines 25-35; column 18, lines 20-30; delete

"

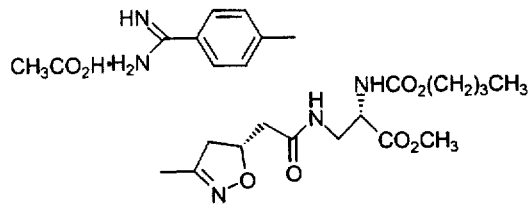

"

and insert

--

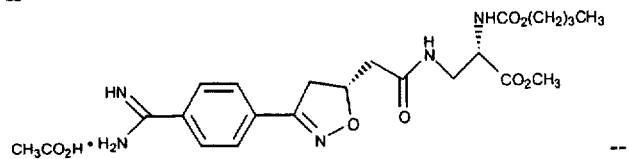

--

At column 12, line 29, delete "Compound ()" and insert --Compound (I)--

At column 14, line 44, delete "IN" and insert --1N --

UNITED STATES PATENT AND TRADEMARK OFFICE
CERTIFICATE OF CORRECTION

PATENT NO. : 6,136,833

ISSUED : October 24, 2000

INVENTOR(S) : Sherif Ibrahim Farag Badawy, Donna Lynn Gilbert

It is certified that error appears in the above-identified patent and that said Letters Patent are hereby corrected as shown below:

At column 3, line 27, delete "lc" and insert -- la --

Signed and Sealed this

First Day of May, 2001

Attest:

NICHOLAS P. GODICI

Attesting Officer      Acting Director of the United States Patent and Trademark Office